United States Patent [19]

Amano et al.

[11] 4,298,599

[45] Nov. 3, 1981

[54] NOVEL ANTIBIOTIC BN-235 SUBSTANCE, AND PROCESS FOR THE PRODUCTION THEREOF

[75] Inventors: Shoichi Amano, Kawasaki; Shinji Miyadoh, Yokohama; Saeko Takahashi, Tokyo; Norio Ezaki, Yokohama; Tomizo Niwa, Yokohama; Yujiro Yamada, Yokohama, all of Japan

[73] Assignee: Meiji Seika Kaisha, Ltd., Tokyo, Japan

[21] Appl. No.: 186,793

[22] Filed: Sep. 12, 1980

[30] Foreign Application Priority Data

Sep. 12, 1979 [JP] Japan .................... 54-116200

[51] Int. Cl.$^3$ ............................................. A61K 35/00
[52] U.S. Cl. ..................................... 424/119; 435/170
[58] Field of Search ........................ 435/170; 424/119

[56] References Cited

U.S. PATENT DOCUMENTS 3,803,306  4/1974  Kunstmann et al. ............... 424/119

*Primary Examiner*—Jerome D. Goldberg
*Attorney, Agent, or Firm*—Sughrue, Mion, Zinn, Macpeak and Seas

[57] ABSTRACT

A novel antibiotic BN-235 substance and a process for making it are described, wherein the hydrochloride thereof has the following properties:

Elemental analysis values:
  carbon 55.44%
  hydrogen 6.41%
  nitrogen 9.02%
  chlorine 12.01%
  oxygen 17.12% (balance)
Molecular weight: about 520 (by the vapor pressure method)
Melting point: 230° to 232° C. (decomp.)
Ultraviolet absorption spectrum: shown in FIG. 1
Infrared absorption spectrum: shown in FIG. 2
Color reactions:
  Positive: ninhydrin and Lemieux
  Negative: Sakaguchi and ferric chloride
Color and form: yellow powder
Solubility: soluble in methanol, ethanol, acetone and water, and insoluble in ether, n-hexane and petroleum ether
Stability: stable at a pH of 2 to 6
Rf values in thin-layer chromatography (silica gel):
  chloroform-methanol (4:1) 0.73
  n-butanol-acetic acid-water (2:1:1) 0.64
Distinction among acidity, neutrality and basicity: basic.

2 Claims, 2 Drawing Figures

NOVEL ANTIBIOTIC BN-235 SUBSTANCE, AND PROCESS FOR THE PRODUCTION THEREOF

BACKGROUND OF THE INVENTION

This invention relates to an antibiotic, and a process for its production. More specifically, this invention relates to a novel antibiotic BN-235 substance, and to a process for producing the novel antibiotic BN-235 substance which comprises cultivating a BN-235 substance-producing strain of the genus Serratia in a culture medium, and isolating and recovering the BN-235 substance from the culture broth.

SUMMARY OF THE INVENTION

It has now been found that a substance which shows a strong antibacterial activity against Gram-positive and Gram-negative bacteria and an antitumor activity is produced in the cultivation product of a strain of the genus Serratia. After isolation of the active substance in pure form from the cultivation product, and examination of its properties, it was found to be a novel antibiotic substance. This active substance is referred to hereinafter as the BN-235 substance.

Thus, the present invention provides a novel antibiotic BN-235 substance having the physical and chemical properties described hereinbelow.

The invention also provides a process for producing the BN-235 substance, which comprises aerobically cultivating a BN-235 substance-producing strain of the genus Serratia, and recovering the BN-235 substance from the culture broth.

DETAILED DESCRIPTION OF THE INVENTION

Figure 1:
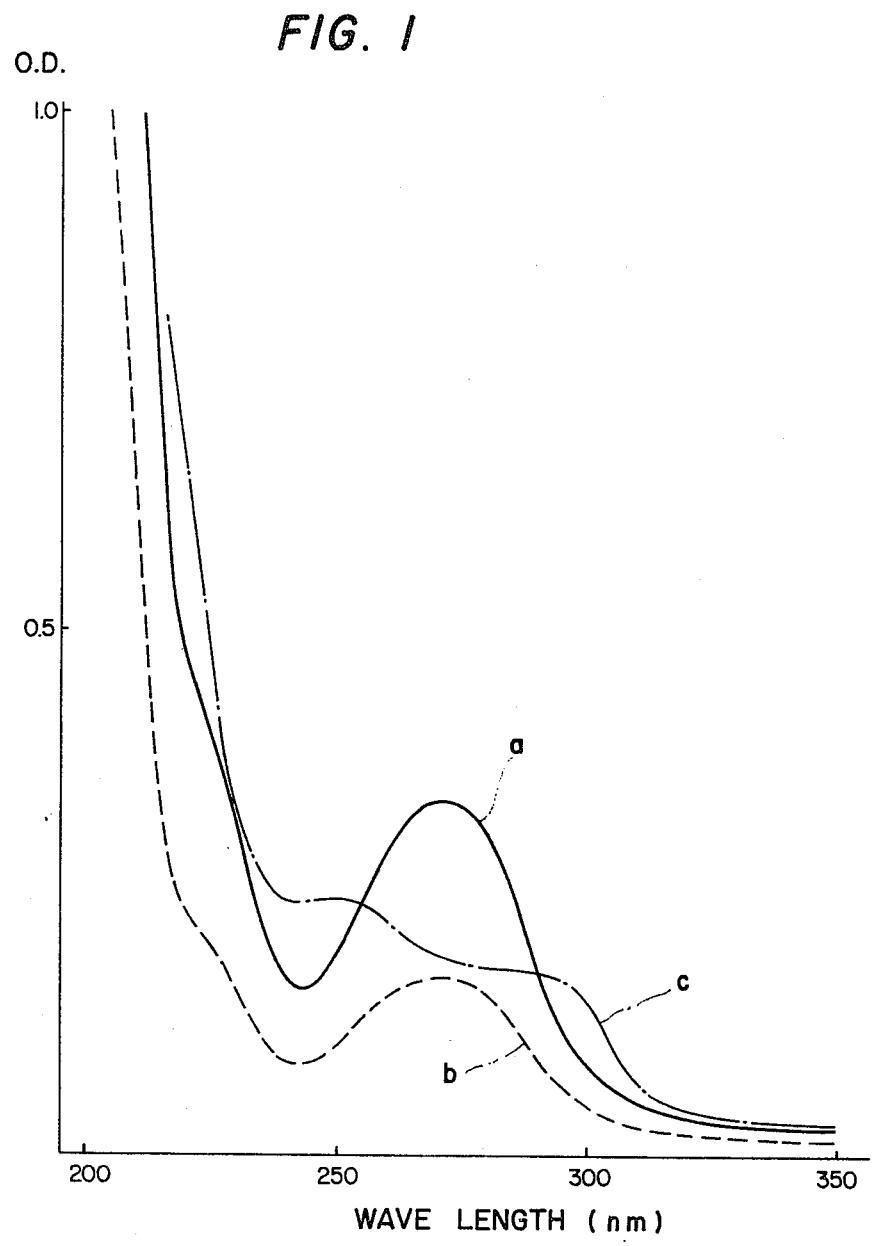
FIG. 1 is an ultraviolet absorption spectrum of the BN-235 substance.

One example of the strain of the genus Serratia used in this invention is Serratia sp. NB-235 isolated from a soil sample collected in Tokyo, Japan. This strain has been deposited with the Fermentation Research Institute, Agency of Industrial Science and Technology, Japan, under the accession number FERM-P No. 4995 and deposited in the American Type Culture Collection (ATCC) under the accession number 31665 on June 24, 1980.

The microbiological characteristics of Serratia sp. BN-235 are as follows:

(a) Morphological characteristics

Cells cultivated on a bouillon agar medium are rod-shaped, with a size of from about 0.4 to 0.6×from 0.8 to 1.5μ, and move with peritrichous flagella. No spore is formed. Gram stain is negative.

(b) Cultural characteristics
  (1) Bouillon agar culture: The bacterial cells are pinkish cream-colored and glistening. Growth abundant. No diffusible pigment is produced.
  (2) Bouillon liquid culture: The entire culture medium becomes turbid. Growth abundant.
  (3) Bouillon gelatin stab culture: Liquefied.
  (4) Litmus milk culture: Liquefied while retaining neutrality.

(c) Physiological characteristics
  (1) Reduction of nitrate: positive
  (2) Denitration reaction: negative
  (3) MR (methyl red) test: negative
  (4) VP (Voges-Proskauer) test: negative
  (5) Production of indole: negative
  (6) Production of hydrogen sulfide: negative
  (7) Hydrolysis of starch: positive
  (8) Utilization of citric acid (the method of Simmons): positive
  (9) Utilizes ammonium salts alone as the nitrogen source (i.e., ammonium salts alone are sufficient but others could be used also).
  (10) Production of pigments: Water-soluble and water-insoluble pigments are not formed.
  (11) Urease: negative
  (12) Oxidase: negative
  (13) Catalase: positive
  (14) β-Galactosidase: positive
  (15) DNases: positive
  (16) Decarboxylation reaction of ornithine: positive
  (17) Potassium cyanide resistance: positive
  (18) Growth range: Grows at from about 10° C. to 37° C., the optimal temperature being about 26° C. to 28° C.; grows at a pH of from about 5 to 8, the optimal pH being about 6.
  (19) Facultatively anaerobic
  (20) OF test (Hugh-Leifson's method): F type
  (21) Requirement of growth factors: negative
  (22) Utilization of carbon sources
    (i) D-glucose: acid-production, positive; gas generated in a very small amount
    (ii) D-mannose: acid-production, positive
    (iii) Inositol: weakly positive
    (iv) D-sorbitol: negative
    (v) Rhamnose: positive
    (vi) Saccharose: negative
    (vii) Melibiose: positive
    (viii) Amygdalin: positive
    (ix) Arabinose: positive
    (x) Lactose: acid-production, negative The BN-235 strain having the above microbiological properties was identified in accordance with *Bergey's Manual of Determinative Bacteriology*, 8th Edition, (1974), and the following conclusions were drawn.

(i) This strain has been determined to belong to the family Enterobacteriaceae, in view of the fact that it is a Gram-negative rod-shaped bacterium without formation of spore and with peritrichous movement, is facultatively anaerobic, and shows the physiological properties of being catalase-positive, oxidase-negative and nitrate reduction-positive, and of forming an acid from glucose.

(ii) This strain has been determined to belong to the genus Serratia in view of the fact that it has the physiological property of being positive in tests of β-galactosidase, decarboxylation reaction of ornithine, utilization of citric acid, gelatin liquefaction, KCN resistance and DNases.

(iii) Only one species, *Serratia marcescens,* is described by Bergey as belonging to the genus Serratia. The strain of the present invention has the ability to ferment arabinose, and therefore, does not completely correspond with the strain as described in the Bergey's Manual. Accordingly, the strain of this invention has been named Serratia sp. BN-235.

Variants of Serratia sp. BN-235 strain can be produced by artificial means using ultraviolet light, X-rays, high-frequency waves, radiation, chemicals, etc. All variants of the genus Serratia can be used in this invention so long as they have the ability to produce the BN-235 substance.

Various culture media used in ordinary microbial fermentation processes can be used to cultivate the BN-235 substance-producing strain and to produce and accumulate the BN-235 substance. Glucose, glycerol, sucrose, dextrin, starch, and glucose syrup, for example, can be used as carbon sources. Nitrogen sources that can be used include, for example, peptone, meat extract, bouillon powder, corn steep liquor, soybean cake, wheat germ, fish meal, yeast extract, ammonium sulfate, and ammonium chloride. Inorganic salts such as sodium chloride, potassium chloride and calcium carbonate, and heavy metal salts may sometimes be used together. If desired, an anti-foamer may be added to prescribe conditions suitable for the production of the BN-235 substance.

Suitable cultivating methods include a shake-culture method and submerged culture methods, such as a submerged aeration agitation culture method.

The cultivation temperature is selected within the range of 20° C. to 35° C., and a suitable cultivation time is from 20 to 24 hours.

The following procedure is used to assay the BN-235 substance. 2% of mycin agar (a product of Kyoei Seiyaku K.K.) is used as an assay medium. *Bacillus subtilis* ATCC-6633 is used as an assaying bacterium. In the assay of the BN-235 substance under the above conditions by a paper disc method, the logarithm of the concentration of the BN-235 substance and the diameter of a zone of inhibition shows a linear relationship in a concentration range of 12.5 γ/ml to 50 γ/ml, and the BN-235 substance provides an inhibitory zone diameter of 19 to 23 mm in ordinary cultivation (about 37° C., about 18 hours).

The BN-235 substance can be extracted and purified by considering its physical and chemical properties described below. The method shown below is one example of an efficient extraction and purification technique.

Specifically, the solid can be removed by filtration from the culture broth containing the active ingredient. The filtrate is adsorbed onto an adsorbent such as activated carbon, and the active ingredient is eluted with an acidic aqueous acetone or an acidic aqueous lower alcohol. After the elution, the organic solvent is distilled off under reduced pressure. The resulting aqueous layer containing the antibiotic is made weakly alkaline, for example, it is adjusted to pH 8.0, and extracted with n-butanol, ethyl acetate, or the like. The extract is transferred to and dissolved in acidic water. The resulting aqueous layer is again made weakly alkaline, and extracted with ethyl acetate. The extract is again dissolved in acidic water, and lyophilized. A yellow powder of the BN-235 substance in nearly pure form is thereby obtained. As required, a more pure BN-235 substance may be obtained by subjecting the product to chromatography using a suitable adsorbent, ion exchange resin, cellulose, silica gel, alumina and gel filtration agent and using a suitable solvent. For example, the resulting yellow powder of the BN-235 substance is dissolved in water and the resulting aqueous solution is charged to a column of a cationic ion exchange resin (for example, Amberlite CG-50 H form (a product of Rohm and Haas Co.)). The column is washed with water, and eluted with a dilute aqueous acetic acid solution to obtain active fractions. The active fractions are collected and concentrated under reduced pressure. The concentrated solution is charged to a column of DEAE-Sephadex A-25 (a product of Pharmacia Co., Sweden) and developed with water to obtain active fractions. The active fractions are concentrated under reduced pressure and then lyophilized. A yellow powder of the BN-235 substance in almost pure form is thereby obtained. If desired, the BN-235 substance in pure form can be obtained by further subjecting the lyophilized product to chromatography using alumina (a product of M. WOELM Co., Germany) and ethanol as a developing solvent followed by concentration under reduced pressure and lyophilization.

The physical and chemical properties of the hydrochloride of the BN-235 substance are shown below.

Figure 2:
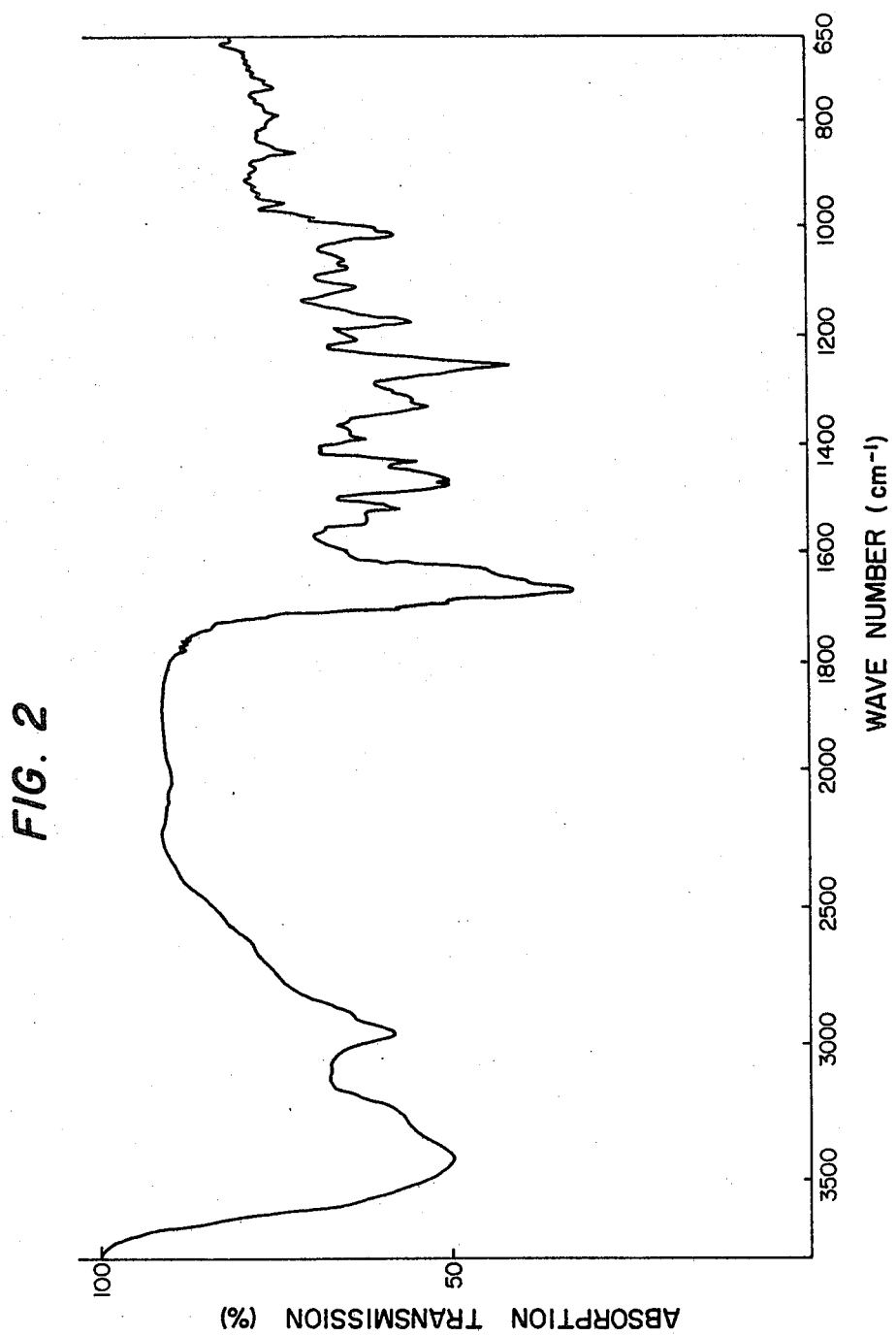
FIG. 2 is an infrared absorption spectrum of the BN-235 substance measured by using a KBr tablet of the present substance.

(1) Color and form: yellow powder
(2) Elemental analysis:
   Carbon 55.44%
   Hydrogen 6.41%
   Nitrogen 9.02%
   Chlorine 12.01%
   Oxygen 17.12% (balance)
(3) Molecular weight: 520 (vapor pressure method)
(4) Melting point: 230°-232° C. (decomp.)
(5) Ultraviolet absorption spectrum: as shown in FIG. 1, determined in aqueous solutions (10 μg/ml), a represents the spectrum obtained in pure water, b represents the spectrum obtained in 0.1 N hydrochloric acid, and c represents the spectrum obtained in 0.1 N sodium hydroxide.
(6) Infrared absorption spectrum: The absorption spectrum, as determined using the KBr tablet method, is shown in FIG. 2 with absorption bands at 3420, 2960, 1670, 1520, 1480, 1460, 1430, 1390, 1330, 1250, 1200, 1160, 1100, 1080, 1060, 1005, 980, 950, 850, 780, 740 cm$^{-1}$.
(7) Solubility: soluble in methanol, ethanol, acetone and water, and insoluble in ether, n-hexane and petroleum ether
(8) Specific rotation:
   $[\alpha]_D^{25} = -77.8$ (C=1, methanol)
(9) Color reaction: positive with ninhydrin and Lemieux, and negative with Sakaguchi and ferric chloride
(10) Stability: stable at a pH of 2 to 6
(11) Distinction among acidity, neutrality and basicity: a basic substance
(12) Rf values in silica gel thin-layer chromatography:
   Chloroform-methanol (4:1) 0.73
   n-Butanol-acetic acid-water (2:1:1) 0.64

The minimum growth inhibitory concentrations of the BN-235 substance against various microorganisms were measured by an agar dilution method using a nutrient agar (a product of Difco) as an assay culture medium, and the results are tabulated below.

| Minimum Inhibitory Concentration by the Agar Dilution Method | |
| --- | --- |
| Test Microorganisms | Minimum Growth Inhibitory Concentration (μg/ml) |
| Staphylococcus aureus FDA 209-p JC-1 | 0.20 |
| Bacillus subtilis (ATCC 6633) | 3.13 |
| Escherichia coli NIHJ JC-2 | 0.39 |
| Salmonella typhi 0-901-W | 0.20 |
| Shigella dysenteriae Shigae | 0.39 |
| Proteus vulgaris J-0001 | 50 |
| Pseudomonas aeruginosa IFO 3080 | 6.25 |
| Pseudomonas cepacia M-0527 | 0.39 |
| Streptococcus faecalis (ATCC 8043) | 1.56 |
| Vibrio percolens | 0.78 |
| Candida albicans | >100 |

In an acute toxicity test using mice, intravenous administration of the BN-235 substance in a dosage of 10 mg/kg caused 50% of the mice to die. When the dosage was changed to 25 mg/kg, all the mice died.

As is clear from the above antibacterial spectrum, the antibiotic BN-235 of this invention has a strong antibacterial activity against Gram-positive and Gram-negative bacteria, and therefore can be used for therapeutic purposes and as germicides or disinfectants for agricultural chemicals and veterinary medicines.

The treatment effect of the BN-235 substance (intraperitoneally administered for three consecutive days) against lymphocytic leukemia P-388 ($1.2 \times 10^6$ cells were intraperitoneally transplanted into $CDF_1$ mice) was examined. As a result, it was found that at a dosage of 1 mg/kg/day, the BN-235 substance was found to have an antitumor activity corresponding to an increase in life span (ILS) of 115%. The antibiotic of this invention can exhibit an effect of increase in life span of mice and other similar mammals with tumors.

EXAMPLE 1

Twenty liters of a fermentation medium containing 1.5% glucose, 1.0% fish meal, 0.5% ammonium chloride and 0.5% calcium carbonate, and having a pH of 7.0 was charged into two 30-liter jar fermentors, sterilized at 120° C. for 15 minutes, and cooled. Serratia sp. BN-235 strain (FERM-P No. 4995) pre-cultivated for 20 hours in the same culture medium in a Sakaguchi flask were inoculated in the fermentation media. The strain was cultivated for 24 hours at 28° C., an agitation rate of 200 rpm and an air flow rate of 20 liters/min., to obtain culture broth of 35 liters having a BN-235 substance concentration of 15 μg/ml.

EXAMPLE 2

The solid was removed from 35 liters of the culture broth obtained in Example 1, and 500 g of chromatographic activated carbon (a product of Wako Pure Chemical Co., Ltd.) was added to the culture filtrate. The mixture was stirred for 30 minutes to cause adsorption of an active component. The activated carbon was washed with water, and packed in a column. The column was eluted with 50% aqueous acetone (pH 3.0) to obtain the active ingredient. Eight liters of active fractions were collected and concentrated under reduced pressure to obtain 2 liters of a concentrate. The pH of the concentrate was adjusted to 8.0 with 6 N sodium hydroxide, and it was extracted with the same volume of ethyl acetate. The extract was back-extracted with 500 ml of acidic water, and adjusted to pH 8.0 with 1 N sodium hydroxide. It was then extracted with the same volume of ethyl acetate. Again, the extract was back-extracted with 50 ml of acidic water (pH 4.0). The extract was concentrated to 10 ml under reduced pressure, and lyophilized to obtain 130 mg of the BN-235 substance as a yellow powder.

EXAMPLE 3

The solid was removed from 35 liters of another culture broth obtained as in the case of Example 1, and 500 g of chromatographic activated carbon (a product of Wako Pure Chemical Co., Ltd.) was added to the residue. The mixture was agitated for 30 minutes to cause adsorption of an active ingredient. The activated carbon was washed with water, and packed into a column. The column was eluted with 50% aqueous acetone (pH 3.0) to obtain an active ingredient. Eight liters of active fractions were collected and concentrated under reduced pressure to obtain 4 liters of a concentrate. The concentrate was neutralized, and charged onto a column (600 ml) of Amberlite CG 50 (H) (a product of Rohm and Haas Company) to cause adsorption of an active ingredient. The column was washed with water, and eluted with 0.4 N acetic acid to obtain the active ingredient. Two liters of active fractions were collected, and concentrated under reduced pressure to 100 ml. The concentrate was charged onto a column (1.1 liters) of EDAE Sephadex A-25 (a product of Pharmacia Co.) and developed with water. 600 ml of active fractions were concentrated to 10 ml under reduced pressure, and lyophilized to obtain 370 mg of a partially purified product of the BN-235 substance. The purified lyophilized product was dissolved in 1 ml of ethanol, and charged onto a column (15 ml) of alumina (a product of M. WOELM, ESCHWEGE, GERMANY), previously packed with ethanol, and developed with ethanol. The active fractions were concentrated to dryness under reduced pressure to obtain 200 mg of the BN-235 substance as a yellow powder.

While the invention has been described in detail and with reference to specific embodiments thereof, it will be apparent to one skilled in the art that various changes and modifications can be made therein without departing from the spirit and scope thereof.

What is claimed is:

1. An antibiotic BN-235 substance, the hydrochloride of which has the following properties:
    Elemental analysis values:
        Carbon 55.44%
        Hydrogen 6.41%
        Nitrogen 9.02%
        Chlorine 12.01%
        Oxygen 17.12% (balance)
    Molecular weight: about 520 (by the vapor pressure method)
    Melting point: 230° to 232° C. (decomp.)
    Ultraviolet absorption spectrum: shown in FIG. 1
    Infrared absorption spectrum: Absorption bands at 3420, 2960, 1670, 1520, 1480, 1460, 1430, 1390, 1330, 1250, 1200, 1160, 1100, 1080, 1060, 1005, 980, 950, 850, 780, 740 cm$^{-1}$ and absorption spectrum as shown in FIG. 2 as determined using the KBr tablet method,
    Color reactions:
        Positive: ninhydrin and Lemieux
        Negative: Sakaguchi and ferric chloride
    Color and form: yellow powder Solubility: soluble in methanol, ethanol, acetone and water, and insoluble in ether, n-hexane and petroleum ether Specific rotation:

$[\alpha]_D^{25} = -77.8$ (C=1, methanol)

Stability: stable at a pH of 2 to 6

Rf values in thin-layer chromatography (silica gel):
  Chloroform-methanol (4:1) 0.73
  n-Butanol-acetic acid-water (2:1:1) 0.64

Distinction among acidity, neutrality and basicity: basic.

2. A process for producing BN-235 substance as in claim 1, which comprises aerobically cultivating Serratia sp. BN-235 (FERM-P No. 4995, ATCC No. 31665) in a culture medium containing assimilable carbon and nitrogen sources at a temperature of from about 10° C. to 37° C. and a pH of from about 5 to 8, and recovering the BN-235 substance from the culture broth.

* * * * *